United States Patent [19]

Gullans et al.

[11] Patent Number: 5,773,213
[45] Date of Patent: Jun. 30, 1998

[54] METHOD FOR CONDUCTING SEQUENTIAL NUCLEIC ACID HYBRIDIZATION STEPS

[75] Inventors: Steven R. Gullans, Natick; Ryoji Kojima, Boston; Jeffrey Randall, Acton, all of Mass.

[73] Assignee: Brigham & Women'S Hospital, Boston, Mass.

[21] Appl. No.: 254,811

[22] Filed: Jun. 6, 1994

[51] Int. Cl.[6] .......................... C07H 21/02; C07H 21/04; C12P 19/34; C12Q 1/68

[52] U.S. Cl. .......................... 435/6; 435/91.1; 435/91.2; 536/20.32; 536/24.33

[58] Field of Search .............................. 435/6, 91.1, 91.2, 435/810; 935/77, 78; 536/24.32, 24.33

[56] References Cited

U.S. PATENT DOCUMENTS

| | | | |
|---|---|---|---|
| 5,057,410 | 10/1991 | Kawasaki et al. | 435/6 |
| 5,210,015 | 5/1993 | Gelfand et al. | 435/6 |
| 5,262,311 | 11/1993 | Pardee et al. | 435/91.2 |

OTHER PUBLICATIONS

Blanchard et al. PCR Methods and Applications 2: 234–240, 1993.
David Bauer et al., "Identification of Differentially Expressed mRNA Species by an Improved Display Technique (DDRT–PCR)", *Nucleic Acids Research*, vol. 21, No. 18, pp. 4272–4280, 1993.
Peng Liang et al., "Differential Display and Cloning of Messenger RNAs from Human Breast Cancer versus Mammary Epithelial Cells", *Cancer Research*, vol. 52, pp. 6966–6968, Dec. 15, 1992.
Peng Liang et al. "Differential Display of Eukaryotic Messenger RNA by Means of the Polymerase Chain Reaction", *Science*, vol. 257, pp. 967–971, Aug. 14, 1992.
Ruth Sager et al., "Identification by Differential Display of Alpha 6 Integrin as a Candidate Tumor Suppressor Gene", *The FASEB Journal*, vol. 7, pp. 964–970, Jul. 1993.
John Welsh et al., "Arbitrarily Primed PCR Fingerprinting of RNA", *Nucleic Acids Research*, vol. 20, No. 19, pp. 4965–4970, 1992.
John Welsh et al., "Fingerprinting Genomes using PCR with Arbitrary Primers", *Nucleic Acids Research*, vol. 18, No. 24, pp. 7213–7218, 1990.
Wayne M. Barnes, "PCR Amplification of up to 35–kb DNA with High Fidelity and High Yield from λ Bacteriophage Templates", *Proc. Natl. Acad. Sci. USA*, vol. 91, pp. 2216–2220, Mar. 1994.

(List continued on next page.)

*Primary Examiner*—Stephanie W. Zitomer
*Assistant Examiner*—Paul B. Tran
*Attorney, Agent, or Firm*—Kenyon & Kenyon

[57] ABSTRACT

A method for conducting sequential nucleic acid hybridization steps is described, whereby the ability of earlier-used primers or probes to participate in subsequent hybridization steps can be minimized, even though the differences between primer lengths are relatively small. It also relates to a rapid and quantitative method for the sequential synthesis of polynucleotide sequences by using a plurality of oligonucleotide primers, with the earlier utilized primers causing a minimum of interference with the subsequent primed synthesis reactions, yet without the need for intermediate purification steps. One preferred embodiment described is a method for differential display reverse-transcription polymerase chain reaction (DDRT-PCR), wherein complementary DNAs (cDNAs) are first synthesized using oligo-dT-primed reverse transcription (RT), and selected subsets of said cDNAs are then amplified using a second primer in a polymerase chain reaction (PCR), with a minimum degree of background being caused in the PCR step by residual amounts of the oligo-dT primer.

17 Claims, 9 Drawing Sheets

OTHER PUBLICATIONS

Zhiqiang Zou et al., "Maspin, a Serpin with Tumor–Suppressing Activity in Human Mammary Epithelial Cells", *Science*, vol. 263, pp. 526–529, Jan. 28, 1994.

Caetano–Anolles G., Bassam, B.J., Gresshoff, P.M., "Enhanced Detection of Polymorphic DNA by Multiple Arbitrary Amplicon Profiling of Endonuclease–digested DNA: Identification of Markers Tightly Linked to the Supernodulation Locus in Soybean" *Molecular & General Genetics*, 241 (1–2):57–64, Oct. 1993. (Abstract).

Caetano–Annolles G., Bassam B.J., Gresshoff P.M. "Primer–template Interactions during DNA Amplification Fingerprinting with Single Arbitrary Oligonucleotides", *Molecular & General Genetics*, 235 (2–3):157–65, Nov. 1992. (Abstract).

Eskew D.L., Caetano–Anolles G., Bassam, B.J., Gresshoff P.M., "DNA Amplification Fingerprinting of the Azolla–Anabaena Symbiosis", *Plant Molecular Biology*, 21 (2): 363–73, Jan. 1993. (Abstract).

Ernst S. Kawasaki, "Amplification of RNA", *PCR Protocols: Guide to Methods and Applications*,Academic Press, pp. 21–27, 1990.

Product Review, "New Twists in DNA Technology", *Nature*, vol. 361, p. 567, 11 Feb. 1993.

Peng Liang and Arthur B. Pardee, "Differential Display of mRNA by PCR", *Current Protocols in Molecular Biology*, Supplement 26, pp. 15.8.1 to 15.8.8, 1993.

Kopito, R.R., and H.F. Lodish, "Primary Structure and Transmembrane Orientation of the Murine Anion Exchange Protein", *Nature*, vol. 316, pp. 234–238.

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i i ) HYPOTHETICAL: No ( x i ) SEQUENCE DESCRIPTION: SEQ ID NO:1:

G C C A C C A T G G        10

( 2 ) INFORMATION FOR SEQ ID NO:2:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i i ) HYPOTHETICAL: No ( x i ) SEQUENCE DESCRIPTION: SEQ ID NO:2:

T G C C A C C A T G  G        11

( 2 ) INFORMATION FOR SEQ ID NO:3:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i i ) HYPOTHETICAL: No ( x i ) SEQUENCE DESCRIPTION: SEQ ID NO:3:

A T G C C A C C A T  G G        12

( 2 ) INFORMATION FOR SEQ ID NO:4:

( i ) SEQUENCE CHARACTERISTICS:
        ( A ) LENGTH: 13 base pairs
        ( B ) TYPE: nucleic acid (C) STRANDEDNESS: single
(D) TOPOLOGY: linear (iii) HYPOTHETICAL: No (xi) SEQUENCE DESCRIPTION: SEQ ID NO:4:

GATGCCACCA TGG     13

(2) INFORMATION FOR SEQ ID NO:5:

(i) SEQUENCE CHARACTERISTICS:
(A) LENGTH: 10 base pairs
(B) TYPE: nucleic acid
(C) STRANDEDNESS: single
(D) TOPOLOGY: linear (iii) HYPOTHETICAL: No (xi) SEQUENCE DESCRIPTION: SEQ ID NO:5:

GTCTGGTTCT     10

(2) INFORMATION FOR SEQ ID NO:6:

(i) SEQUENCE CHARACTERISTICS:
(A) LENGTH: 11 base pairs
(B) TYPE: nucleic acid
(C) STRANDEDNESS: single
(D) TOPOLOGY: linear (iii) HYPOTHETICAL: No (xi) SEQUENCE DESCRIPTION: SEQ ID NO:6:

CGTCTGGTTC T     11

(2) INFORMATION FOR SEQ ID NO:7:

(i) SEQUENCE CHARACTERISTICS:
(A) LENGTH: 12 base pairs
(B) TYPE: nucleic acid
(C) STRANDEDNESS: single
(D) TOPOLOGY: linear (iii) HYPOTHETICAL: No (xi) SEQUENCE DESCRIPTION: SEQ ID NO:7:

GCGTCTGGTT CT     12

(2) INFORMATION FOR SEQ ID NO:8:

(i) SEQUENCE CHARACTERISTICS:
(A) LENGTH: 13 base pairs
(B) TYPE: nucleic acid
(C) STRANDEDNESS: single
(D) TOPOLOGY: linear (iii) HYPOTHETICAL: No (xi) SEQUENCE DESCRIPTION: SEQ ID NO:8:

TGCGTCTGGT TCT     13

(2) INFORMATION FOR SEQ ID NO:9:

(i) SEQUENCE CHARACTERISTICS:
(A) LENGTH: 13 base pairs
(B) TYPE: nucleic acid
(C) STRANDEDNESS: single
(D) TOPOLOGY: linear (iii) HYPOTHETICAL: No (x i) SEQUENCE DESCRIPTION: SEQ ID NO:9:

CGAATCCGAG TGA                                                                                          13

(2) INFORMATION FOR SEQ ID NO:10:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (i i i) HYPOTHETICAL: No (x i) SEQUENCE DESCRIPTION: SEQ ID NO:10:

TGCTTCAGCA CTG                                                                                          13

(2) INFORMATION FOR SEQ ID NO:11:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (i i i) HYPOTHETICAL: No (x i) SEQUENCE DESCRIPTION: SEQ ID NO:11:

GACGGACAGC TTC                                                                                          13

(2) INFORMATION FOR SEQ ID NO:12:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (i i i) HYPOTHETICAL: No (x i) SEQUENCE DESCRIPTION: SEQ ID NO:12:

AGCGATACGA GGC                                                                                          13

METHOD FOR CONDUCTING SEQUENTIAL NUCLEIC ACID HYBRIDIZATION STEPS

FIELD OF THE INVENTION

This invention relates to a method for conducting sequential nucleic acid hybridization steps, whereby the effects of earlier-hybridized nucleic acid strands on subsequent hybridization steps can be minimized. It also relates to a rapid and quantitative method for the sequential synthesis of polynucleotide sequences by using a plurality of oligonucleotide primers, with the earlier utilized primers causing a minimum of interference with the subsequent primed synthesis reactions, yet without the need for intermediate purification steps. In a preferred embodiment, the invention relates to a method for differential display reverse-transcription polymerase chain reaction (DDRT-PCR), wherein complementary DNAs (cDNAs) are first synthesized using oligo-dT-primed reverse transcription (RT), and selected subsets of said cDNAs are then amplified using a second primer in a polymerase chain reaction (PCR), with a minimum degree of background being caused in the PCR step by residual amounts of the oligo-dT primer.

BACKGROUND OF THE INVENTION

1. The need for successive hybridizations

Many of the methods for manipulating nucleic acids that are the foundation of modern molecular genetics take advantage of the fact that short pieces of nucleic acid will specifically hybridize to longer nucleic acid strands. The purposes for which hybridization is used are many, and all are within the scope of the present invention. These purposes can be divided into three basic categories.

A first category is the use of hybridization to detect the presence of a particular DNA or RNA sequence. In such a method, a generally shorter piece of DNA or RNA is usually labeled in some manner, such as by incorporation of a radio-label such as the radioactive isotope of phosphorous, $P^{32}$ or by the addition of a fluorescent group. This "labeled probe" is then added to the sample of DNA or RNA to be "probed". If a sequence exists in that DNA or RNA that is complementary to the sequence of the labeled probe, then the probe hybridizes, or sticks, to that specific sequence. When the generally smaller probe is then washed away or otherwise removed under conditions that the DNA or RNA to be probed does not wash away, the specifically bound probe also does not wash away, and can be detected, for example, in the case of a radio-labeled probe, by exposing the DNA or RNA sample to an X-ray film, or in the case of a fluorescently labeled probe, by irradiating the sample with an excitation beam and examining the sample for fluorescence.

A second category of uses for hybridization is in methods for purifying DNA or RNA having particular sequences. For example, such a method can be used to purify messenger RNA (mRNA) from samples of RNA that are extracted from cells or tissues. Total RNA extracts contain three major types of RNA: ribosomal RNA (rRNA), which is the major component; transfer RNA (tRNA); and mRNA. Since messenger RNA is used by cells as a template for the synthesis of proteins, it is of the most interest to many researchers. Fortunately, virtually all mRNA strands have a "poly-A tail"; that is, one end of each strand contains a sequence of all adenosines: AAAAAAAA . . . . Since adenosine base pairs with thymine, this tail will hybridize with an oligo-dT strand: TTTTTTTT . . . . Such oligo-dT strands can thus be easily used to purify mRNA. By immobilizing the oligo-dT on a resin and packing that resin into a column, for example, it is a simple matter to pass a total RNA extract through that column under hybridizing conditions; the poly-A tails of the mRNA stick to the oligo-dT, and the mRNA is held to the column, while the rRNA and tRNA are washed away. The mRNA can then be recovered by placing the column resin under conditions that disfavor hybridization, most typically by passing a solution containing a high salt concentration through the column.

A third category of uses for hybridization in molecular genetics is as a "primer" for an enzymatic action, most notably for synthesis of a complementary strand of RNA or DNA. For example, an oligo-dT primer can be used as a starting point for the enzyme reverse transcriptase, which in the presence of nucleic acid monomers will make a strand of DNA that is complementary to the mRNA (known as a cDNA). cDNAs are widely used in research because DNA has a greater chemical stability than RNA. Also, as further described hereinbelow, researchers often use such reverse transcription to prepare cDNAs and then simply digest away all RNA; this obviates the need to purify mRNA as described in the paragraph above.

Another important example of this third type of hybridization technique is the polymerase chain reaction, or PCR. In this method, a primer serves as a starting point for the synthesis of a strand of DNA by the enzyme Taq polymerase. After this synthesis is complete, the sample is heated until the original strand and the new strand "melt" apart; the sample is then cooled until the excess of primers in the sample can hybridize to the longer "parent" strands. Since Taq polymerase is not easily destroyed by heat, it can once again synthesize new strands from those primer starting points. Thus, by simply cycling the heat of the sample, it is possible to make a tremendous quantity of DNA. By selecting the primer sequences carefully, it is possible to only amplify those strands of greatest interest, such that eventually the presence of the non-target strands becomes negligible. Furthermore, by labeling the primers or amplified products, e.g., with $P^{32}$ or $S^{35}$, it is possible to not only amplify the strands of interest, but to label them, too.

Because hybridization methods are so important in molecular genetics, it is not at all unusual to carry out several hybridizations, one right after the other. For example, it is not unusual to purify mRNA on an oligo-dT column, and then amplify the resulting mRNA with PCR. Another example, one which has been of particular interest to us, has been the use of reverse transcription followed by PCR. Of course, there are many other examples of sequential hybridization reactions that are known or can be easily imagined by those skilled in the art of molecular genetics.

2. Difficulties in successive hybridization

If a researcher wishes to use the same primer or probe for all successive hybridization reactions, then residual amounts of probe or primer from the first hybridization will be of little problem in subsequent steps. However, it is often the case that different primers or probes are used in successive hybridization reactions. In such instances, any residual amounts of the first probe or primer will cause an artifact or background reaction in subsequent hybridization steps. This is of particular concern when one or several steps are PCR reactions; because of the logarithmic amplification that occurs in such reactions, even minute amounts of contaminating primer can cause very significant background signals that can obscure or otherwise interfere with the desired signal.

There are several ways that have been used in the prior art to eliminate or reduce the background signal that might be caused by primer or probe remaining after a prior hybridization step. The most common is the use of ethanol precipitation, in which DNA is precipitated by the addition of ethanol to the sample and cooling the sample in a dry ice bath. Long DNA strands precipitate under such conditions, but smaller ones, including most probes and primers, do not. The DNA can then be precipitated by centrifugation, and the primer or probe in the supernatant can be decanted away. The DNA pellet is then usually washed with cold ethanol to get rid of remaining primer or probe.

Unfortunately, ethanol precipitation has substantial drawbacks. One drawback is that where small DNA target molecules are involved, ethanol precipitation may cause substantial losses of the DNA being studied. Even with large DNA molecules there are some losses. Perhaps most problematic, however, is the fact that losses in ethanol precipitation will vary between different DNA molecules that may be present in the sample. Although these differential losses are most likely due to differences in length of the different strands, it is impossible to calculate relative losses. This means that the relative concentration of DNA strands that existed in a sample prior to ethanol precipitation cannot be accurately calculated. In experiments such as those described below, where a researcher wishes to determine if a particular DNA strand is present in greater or lesser quantity in samples derived from a diseased individual when compared to the quantity present in samples prepared from a healthy individual, such differential losses can make meaningful analysis of the results impossible. Relative concentrations of DNA or RNA species within the same sample also cannot be reliably quantified.

Another prior art method for eliminating primer carryover is to separate the longer DNA strands of interest by electrophoresis through a polyacrylamide gel or agarose gel. Since these separate by size, the longer strands of interest can be visualized, and the bands of interest can be cut out and extracted. However, this method also causes considerable losses, and cannot be conveniently used when complex mixtures of target nucleic acid strands are of interest. Because losses between treated samples are not uniform, this method also prevents the researcher from comparing relative quantities of DNA or RNA between samples or within a given sample.

3. Successive hybridization in gene screening methods

One of the most important and active areas of molecular genetics research is the search for genes that cause or are otherwise involved in the onset or course of human diseases. Unfortunately, fewer than 5% of all mammalian genes have been identified as of this time. In the past few years, considerable attention and financial resources have been directed towards sequencing the human genome, which is expected to be completed in the next few years. An alternative, more rapid approach that is also being used is to isolate and sequence cDNAs, as these are related to the expressed genes, and not to the 97% or so of the total human genome that is not expressed. Since diseases are most likely caused by problems with genes that are actively expressed rather than with those that are dormant, this may prove to be a more rapid approach to understanding the genetic basis of human diseases. However, neither sequencing the whole genome nor sequencing cDNAs will ascribe any relative significance to a particular gene as it relates to human disease; even with this information it will not be readily apparent which genes are defective in particular diseases.

Fortunately, there are several approaches to finding a gene or genes that play an important role in a particular human disease. For clearly inherited diseases, one can study DNA samples from multiple family members and use gene mapping techniques to find a gene defect common to those demonstrating symptoms of the disease. This approach, known as "positional cloning", has been used in studying the genetic basis for cystic fibrosis and for Huntington's disease. Another approach that can be used is to first identify the cellular malfunction that leads to the disease symptoms, and then look for the gene or genes that are involved in that particular cellular function in normal cells.

Unfortunately, many of the most widespread and serious human diseases are not associated with a single gene defect, and the cellular malfunctions that cause the disease symptoms are not known, and may in any event be highly complex. Thus, such methods are of little aid to our understanding of diseases such as hypertension, heart disease, and cancer.

One of the problems encountered in examining the DNA of normal and diseased individuals for differences is that the human genome is so vast that there is no easy way to compare them. If fragments of all of the genes, or even all cDNAs, were to be labeled and then separated by size, e.g., by electrophoresis through a DNA sequencing gel, there would be so many different species in those mixtures that only a big "smear" would be seen when the gel was exposed to an X-ray film. There would be so many different sized molecules present that none would be discernable as discreet "bands", and thus no comparison could be made.

A new and potentially very powerful new method has recently been described that allows for such a direct comparison, but allows the genome (or the full compliment of cDNAs) to be subdivided in a way that allows discrete bands to be discerned and compared. This method, known as differential display polymerase chain reaction (DD-PCR), now makes it possible to detect genes and cDNAs that are related to the disease state in a single individual, without the need to know what cellular systems are involved.

In DD-PCR, primers are chosen arbitrarily; that is, one simply makes up a sequence for a primer, and then synthesizes that primer, for example, by using a commercially available DNA synthesizing machine. The primer is then labeled, and is used to prime a PCR reaction, using a population of cDNAs or genomic DNA fragments as the template. Based upon the length of the primer chosen, there is a statistically calculable likelihood that a given strand will have a sequence in it that is complementary to the arbitrarily chosen primer. Thus, when a highly complex target mixture is used, only a small subset of the DNA strands in the mixture will be able to hybridize to the primer and serve as a template for PCR. This allows the researcher to distinguish individual PCR-produced strands, usually by electrophoresis on a DNA sequencing gel, which separates the strands into "bands" that can be visualized by exposing the gel to an X-ray film. If there is a "differential display"—a band occurs in the gel lane corresponding to the normal individual's DNA and not in the gel lane corresponding to the diseased individual's DNA, or vice-versa—the differentially displayed cDNA or gene fragment is potentially involved in the disease. The corresponding bands can be cut out of the gel and the DNA can be extracted, amplified by PCR, and then can be used for further study, for example, by DNA sequencing.

The DD-PCR method is currently most often carried out in a "hit-or-miss" fashion, where the researcher makes up a few arbitrary primers, and hopes that one of them will cause a differential display, thus yielding a DNA strand of further interest. However, it is possible to carry out DD-PCR in a more systematic fashion, in order to search the entire human genome for disease-related genes. In such an approach, a researcher would make up a set of primers that represents the entire spectrum of possible sequences for a primer of the selected length. For each base added to the length of the primer, there are 4 times as many possible sequences; thus, for a ten base pair primer, there are 4×4×4×4×4×4×4×4×4×4 possible sequences, or 1,048,576 possible sequences. By preparing all 1,048,576 possible primers, and then using them all to prime separate PCR reactions, the entire genome could be broken down into 1,048,576 separate analytical groups to be examined for differential display. This formidable task can be reduced substantially by considering that most genes of interest are likely to be at least 1,200 base pairs in length (the average mRNA is about 1200 base pairs, which would theoretically encode for a protein of a maximum of 400 amino acids), and that since a 1200 base pair sequence would hybridize to at least an average of 120 different primers (and potentially many more when overlaps are considered), the number of primers needed to "see" each gene once would be less than about 8500 (1,048,576/120= 8738). The task is further reduced if we look only at cDNAs rather than the whole genome, since it is estimated that a mammalian cell population contains only about 15,000 different mRNA species.

On the other hand, any rational systematic approach to DD-PCR would be far more tedious than any human could likely endure, particularly since each disease state requires that the whole process be done again. And although automation could makes such an approach quite feasible, there have been, until the present invention, a problem with existing DD-PCR methods that has made automation problematic and perhaps even impossible.

The DD-PCR methods that show the greatest promise involves the use of reverse transcription together with a polymerase chain reaction (DDRT-PCR) to identify differentially expressed mRNAs [1, 2, 3, 5]. This focuses the analysis on the expressed genes, which are most likely involved in disease states. Such methods have been used successfully to identify and, in some cases, to clone differentially expressed cDNAs [4,7,8]. Unfortunately, the carry-over contamination of the PCR step with the primer used for reverse transcription causes a background problem of the type that is described more generally in the section above. This carry-over contamination causes undesirable spurious products that result in significant levels of background noise, or smears, when the PCR products are separated using gel electrophoresis. Typically, the cDNAs being used in the PCR reaction have been made by using an oligo-dT primer, and despite efforts to remove this primer, trace amounts remain, and act as primers during the subsequent PCR reaction. As a result, PCR products can be formed from every DNA molecule in the reaction mixture having a corresponding run of nucleotides, resulting in a large number of products having a wide range of molecular weights. These products then produce a broad smear over the tracks of the electrophoretic gel, diminishing or obscuring the desired signal.

Such background noise severely compromises the resolution of the DDRT-PCR technique. The prior art has tried to overcome this limitation in a variety of ways, some of which are described below. However, until the present invention, there has not been a solution to this problem that is wholly satisfactory.

Liang and Pardee [3] made a crucial procedural choice that appears to have been directed at limiting this background problem. Their motivation is apparent from the fact that they explain that their attempts to first purify the mRNA on an oligo-dT column failed due to an insurmountable background problem, which they postulated was caused by oligo-dT leaching from the column. The choice that they made was to use an "anchored" oligo-dT primer both to prime the cDNA synthesis, and also to prime the PCR reaction. The oligo-dT primer has several bases to the 3' end of the oligo-dT stretch, which "anchors" it to the 5' end of the poly-A tail and which also allows for cDNA synthesis from only about $\frac{1}{12}$ of the total population of mRNAs present in the sample.

The secondary use of the reverse transcription primer as the intended primer for the PCR reaction eliminated the possibility of such a background problem. This method has enabled researchers to identify and characterize several tumor suppressor genes [4, 8]. However, the PCR-amplified strands that result from this method all begin at the 5' end of the poly-$A^+$ tail, and extended a maximum of 600 base pairs in the 5' direction. This region is typically polymorphic, often contains repetitive sequences, and, because it generally contains a non-coding region, offers no information regarding the potential function of differentially expressed genes. In addition, because the products are typically short fragments (<600 bp) that can contain repetitive sequences, they often hybridize to multiple mRNA species in a northern blot or to multiple clones in a cDNA library. Although significant methodological improvements have been offered [1, 2], the Liang and Pardee method still has the significant drawback that it preferentially amplifies the non-coding 3' untranslated region (3' UTR) of cDNAs during PCR.

Welsh and co-workers [5] have devised an alternative RT-PCR protocol that also avoids the background problem caused by oligo-dT priming of the reverse transcriptase reaction. In this method, both the RT reaction and the PCR reaction are performed using a single 20-mer random oligodeoxynucleotide primer. By performing the PCR reaction for a few initial cycles with a low hybridization temperature (40° C.) and then increasing the hybridization temperature for the remaining cycles, they were able to detect multiple PCR products which exhibited tissue- and strain-specific differences in expression. The low temperature theoretically allows some mismatches, extending the number of sequences copied; then a higher temperature is used in subsequent PCR cycles, to assure fidelity of the amplification. They recently used this approach to identify an oxidant stress induced mRNA [7]. This method, however, fails to preferentially select mRNA (i.e., it does not specifically targeting poly$(A)^+$ RNA), generates only 10–20 PCR products per reaction, and is unable to easily target and amplify specific genes or gene families because it uses only a single primer.

Another method known as RNA-PCR is used for the amplification of individual target cDNAs where some coding sequence information is known. In this method, as described by Kawasaki [9], a random hexamer oligonucleotide is used to prime reverse transcription of RNA, and primers of about 18 to 22 bases in length are then used to amplify the target cDNA by PCR. This method does not appear to include a purification step between the first and second priming steps. However, from the method and its results as described, it is not clear whether there is significant background caused by the presence of the random hexamer during the subsequent PCR reaction. Since this method is directed towards the isolation of single cDNAs, rather than towards the analysis of complex differential display patterns, it would not be expected to be as sensitive to such background contamination. Furthermore, the PCR primers used in the Kawasaki method, which are about 18 to 22 bases long, would be too long for DDRT-PCR, and would also be too long for many other methods where successive hybridizations would be useful.

Until the present invention, there was no DDRT-PCR method available that was able to search only messenger RNA sequences, and also preferentially search the coding regions, for differences between normal and diseased individuals.

ADVANTAGES AND SUMMARY OF THE INVENTION

The present invention is derived from the surprising discovery that remarkably fine control over the hybridization of primers and probes is possible. Surprisingly, primer or probe length and calculated melting points do not accurately predict how effective they can be in hybridizing to target nucleic acids at given temperatures, and even successive primers of relatively close sizes and melting temperatures can differentially hybridize to DNA when different temperatures or other hybridization conditions are used for the successive hybridization steps. The degree of control that can be achieved is quite remarkable, we have found, even when the lengths of the respective primers differ by only a few bases.

Although successive hybridization steps are often used in molecular genetics, there has been no adequate means of avoiding the effects of carry-over of probes and primers from prior hybridization steps when the sizes of the respective probes and primers are similar. It is therefore one object of the present invention to provide a means for avoiding such background problems.

It is also an object of this invention to provide a means by which it becomes possible to carry out successive hybridization steps and hybridization-dependent reactions with similarly sized probes and primers, without the need to remove probes and primers used in prior steps, thereby eliminating the need for purification between steps, or allowing steps to be effectively combined.

It is still another object of the present invention to conduct a first primed synthetic step and a second primed synthetic step, wherein the primer from the first synthetic step does not function significantly in the second synthetic step, even though the primers are of similar size and are simultaneously present in solution.

The prior art relating to DDRT-PCR described above does not meet the present need for a rapid means for identifying and isolating differentially expressed mRNAs, but without selectively isolating the untranslated region of cDNAs, and that also does not indiscriminately select RNA which is not associated with gene expression.

It is another object of the invention, then, to isolate genes based on their differential expression in a particular disease state. The isolated genes can serve, for example, as markers of disease state, prognosis or treatment.

It is also an object of the present invention to provide an effective reverse transcriptase primer that is capable of hybridizing to the poly (A)$^+$ tail of messenger RNA to prime reverse transcription, while at the same time being substantially ineffective as a primer during subsequent PCR reactions using primers that are less than three times the length of the reverse transcriptase primer.

It is another object of the present invention to provide an RT primer that is effective at a given RT reaction stringency, while being ineffective as a primer at a higher PCR reaction stringency.

It is yet another object of the present invention to provide PCR conditions having sufficient stringency to promote hybridization of a preselected PCR primer to its template, while inhibiting the hybridization of a preselected RT primer, even though those primers are of similar size.

It is a further object of the present invention to provide various combinations of PCR primers and RT primers, wherein the PCR primers will hybridize to a template while the RT primer will not appreciably so hybridize at a preselected stringency, even though the two primers are of similar size.

It is another object of the present invention to provide a method for DDRT-PCR, wherein reverse transcription is carried out on a predetermined fraction of cellular RNA, followed by a PCR reaction carried out on the resulting cDNA, without the primer for the RT reaction contributing to amplification during the subsequent PCR reaction. This allows the selection criteria for the predetermined fraction of RNA to be selected independently from the criteria for amplification.

It is yet another object of the present invention to provide a kit for determining differential gene expression associated with two or more sources.

It is a further object of the present invention to provide a method for DDRT-PCR that is suitable for automation.

It is a still further object of the present invention to provide a DDRT-PCR method that can be used to detect genetic causes of human, animal, and plant diseases, and to detect the effects of such diseases, not only for the purposes of research and diagnosis, but also for the purpose of developing therapies that can be used to treat and prevent such diseases.

It is another object of the invention to provide a method that can allow for the screening of a plurality of genes at the same time.

One advantage of the present invention with respect to the prior work of Liang and Pardee (3) is that the present invention can be practiced such that it does not selectively isolate the terminal 3' untranslated region of the cDNA during PCR. Instead, the method according to the present invention preferentially targets internal cDNA sequences. This means that the technique of the present invention is more likely to lead to isolation of coding regions of the genes and thus, based on homology analysis, offer insight into the potential function of a gene and also possibly identify the disease-related roles of those genes that have been previously studied. This also means that, because the non-coding 3' untranslated regions isolated using prior methods are generally more polymorphic and often contain repetitive DNA sequences, these prior methods yield cDNAs that will be much more difficult to clone and possibly map compared to those generated by the present invention. In addition, the present invention requires one to perform only a single reverse transcription reaction, whereas prior methods require 4 to 12 separate reverse transcription reactions before the entire cellular compliment of mRNA can be screened, adding a level of complexity unnecessary in the method of the present invention. Finally, the coding region of a gene is much less polymorphic than the non-coding region of a gene; that is, there are fewer and less dramatic individual-to-individual differences between coding regions, where "genetic drift" is curtailed due to the need for proper function of the gene product, than there is in non-coding regions. Thus, using the present invention, genetic "fingerprint" patterns will be much less complex to analyze among different individuals in a population of interest, and are more likely to be the result or cause of the disease, and not the result of random "genetic drift".

An advantage of the present invention with respect to the prior work of Welsh and co-workers is that the present invention can be practiced using primers for the RT step that differ from the primers used for the PCR reaction. This allows the use of poly-dT primers in the RT reaction, advantageously resulting in the preferential selection of poly(A)+ RNAs, and thereby eliminating fruitless examination of the much more abundant ribosomal RNA or contaminating genomic DNA. In addition, by using a very non-specific primer for the RT reaction, the present invention has the advantage that only a single RT reaction is necessary, as compared to the potentially hundreds of different RT reactions that are necessary using the highly specific RT primers of Welsh and co-workers. Moreover, the present invention is advantageous as compared to the method of Welsh and co-workers because their RT reaction targets only a small subset of the available mRNAs and the PCR reaction thus fails to amplify as many cDNAs as the present method. In general, the method of Welsh and coworkers detected only about 20 PCR products, some of which may be ribosomal RNA. Consequently, as compared to the present method, in order to analyze the expression of all mRNAs using their method will require one to perform 2 to 5-fold more PCR reactions and thereby run and analyze many more gels. The greater efficiency thus realized by the method of the present invention make it preferable both for manual and for automated methods.

This invention also offers advantages over the method of Kawasaki, in that it allows the use of successive primers of similar size, e.g., using second primers that are less than three times the length of the RT primer.

According to one embodiment of the invention, a series of hybridization steps are conducted under conditions of increasing stringency. Each hybridization step utilizes one or more primers or labels and templates comprised of specific sequences of nucleic acids or their analogues. A first hybridization step is conducted at a preselected level of reaction stringency which allows one or more first primer or label to hybridize to one or more first complementary templates. A second hybridization step is then conducted after adding one or more second primers also selected to hybridize to one or more second templates having complementary sequences. The second primers are selected to hybridize to their corresponding templates under conditions having a degree of stringency wherein hybridization of the first primer to the first template is substantially prevented or markedly reduced; but the second primers may be only slightly longer than the first primers, or may be of the same size but otherwise have a higher binding affinity for the target sequence than the prior primer. Additional hybridization steps can also be subsequently conducted under conditions of even higher stringency after adding additional primers that are slightly longer or otherwise have a higher binding affinity than the prior primers.

In one embodiment of the invention, at least one of the primers is acted upon by a polynucleotide synthetase prior to the change in conditions that disfavors its hybridization to its complementary template, or alternatively, one or more primers or probes hybridized to its complementary template is detected prior to the change in conditions that disfavors that hybridization. Of course, both detection of probes and action of a synthetase can be used in subsequent steps.

In a further embodiment of the invention, a plurality of probes to be used in several successive hybridizations are added to the initial reaction mixture, rather than being added sequentially as the various reactions proceed.

Another embodiment of the invention provides a method for differential display reverse transcription-amplification, comprising the steps of reverse transcribing the mRNA in an RNA sample to produce cDNA by using one or more polynucleotide primers to prime the enzyme reverse transcriptase; and then adding one or more additional primers that are slightly longer than the polynucleotide primers of the first step, and using said primers to amplify segments of the template CDNA under conditions which favor hybridization of the longer primers to the cDNA, but disfavor hybridization between the shorter primers used for reverse transcription and said cDNA template.

In another embodiment, the above procedure is carried out on two independent sources of cellular RNA, and the PCR products derived from the two sources are separated and compared.

In still another embodiment of the invention, the cDNA primers are short strands of oligo-dT which prime the reverse transcription of messenger RNA to cDNA. In yet another embodiment, the RT primers are short strands of random nucleotides.

In another embodiment, the reverse transcription reaction is conducted using oligodeoxynucleotides containing about 6 to 8 bases to produce a plurality of cDNA templates at 37° C. Then, a PCR reaction is conducted on the cDNA templates, each at a temperature ranging from about 400 to 600 using 1 to 3 different oligodeoxynucleotides containing about 10 to 14 monomers.

In yet another embodiment, the PCR amplification products are separated on a molecular weight basis using gel electrophoresis.

In a particularly preferred embodiment of the present invention, the various reactions and size separations required for DDRT-PCR by the method of the present invention are carried out substantially by automated machines, for example, automated DNA sequencing machines and the like.

Still another embodiment of the present invention provides a kit for differential display reverse transcription-amplification comprising a first primer, preferably oligo-dT or an arbitrary polynucleotide, and additionally one or more probes that are slightly longer than said first primer. The kit preferably also includes the enzyme reverse transcriptase and reaction buffer suitable for reverse transcription using said first primer and said reverse transcriptase, as well as dNTPs in levels optimized to allow for the completion of both the reverse transcription and the amplification, and also reagents and enzymes needed to carry out the polymerase chain reaction (PCR), said reagents being formulated such that PCR will be primed by the slightly longer second primers, but will not be substantially primed by the first primer.

The appended claims are hereby incorporated by reference as a further enumeration of preferred embodiments. Other objects and advantages of the invention and alternative embodiments will readily become apparent to those skilled in the art, particularly after reading the detailed description, materials and methods, and examples set forth below.

DETAILED DESCRIPTION OF THE INVENTION

Figure 1:
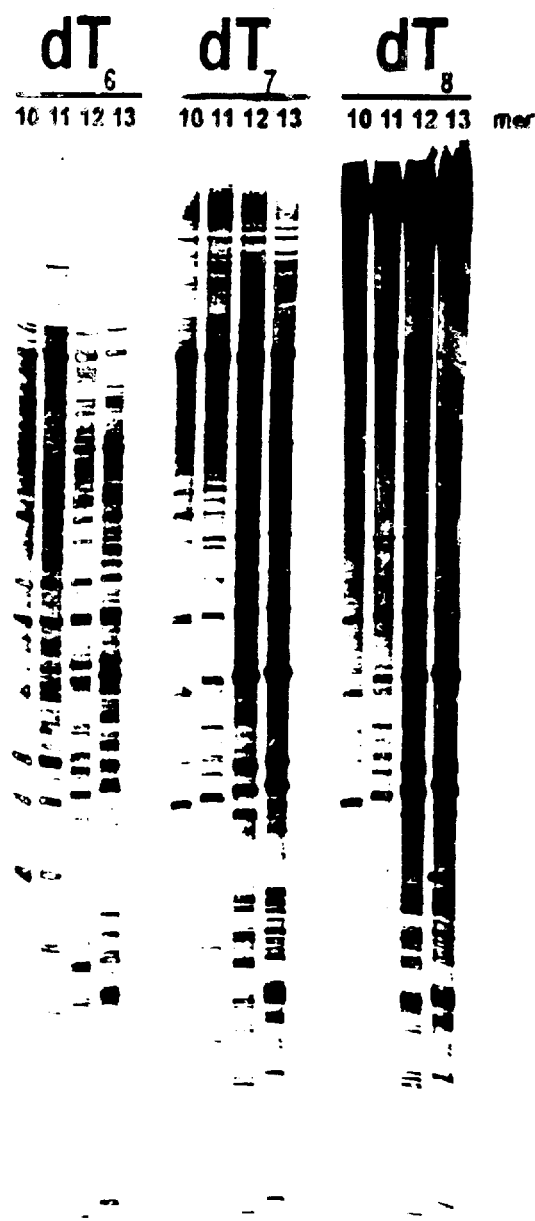
FIG. 1 is an autoradiograph showing the effect of performing the RT reaction using different length oligo-dTs and also the effect of performing the PCR reaction using arbitrary oligodeoxynucleotides of different lengths.

As stated above, the present invention is derived from the surprising discovery that remarkably fine control over the hybridization of primers and probes is possible, and that even successive primers of relatively close sizes can differentially hybridize to DNA when different temperatures or other differences in hybridization conditions are used for the successive hybridization steps. For example, we have found that an oligo-dT 7-mer could be used to prime reverse transcription using a hybridization temperature of 37° C., and arbitrary 10 to 13-mers could be then be used to prime PCR using a hybridization temperature of 40° C., with little or no background being caused by the continued presence of the oligo-dT 7-mer.

In order to facilitate a full and complete understanding of the present invention, it is important to note that all terms used herein are intended to have the same meaning as generally ascribed to those terms by those skilled in the art of molecular genetics. The references cited herein are incorporated by reference.

Furthermore, in order to provide greater clarity and to simplify the description and discussion of the present invention, certain terms have been used in ways that may differ in some respects from their most common usage, and some terms have been adopted or adapted that are not well known in the art. These are described hereinbelow.

By the term "synthetic step" we mean any procedure utilizing: (1) a template comprising a sequence of nucleic acids, (2) a primer comprising a sequence of nucleic acids that is complementary to the template, (3) a group of nucleotide monomers, and (4) a polymerase enzyme for catalyzing the addition of the monomers to the primer based on complementary sequences on the template. Such synthetic steps include reverse transcription and PCR, and also a whole host of other reactions that are well known to those skilled in the art.

In using the terms "nucleic acid", RNA, DNA, etc., we do not mean to limit the chemical structures that can be used in particular steps. For example, it is well known to those skilled in the art that RNA can generally be substituted for DNA as a template, and as such, the use of the term "DNA" should be read by those skilled in the art to include this substitution. In addition, it is known that a variety of nucleic acid analogues and derivatives can be made and will hybridize to one another and to DNA and RNA, and the use of such analogues and derivatives is also within the scope of the present invention.

In a number of instances we refer to the use of "arbitrary" nucleic acid sequences, or "arbitrarily synthesized" sequences. By this term we mean that these nucleic acid sequences were simply "made up". They may be fully or partially random, although there is generally no need to provide mathematical randomization. On the other hand, such sequences may comprise or contain full or partial nucleic acid sequences that are known. For example, certain codons representing certain amino acid encoding motifs might be included, or other sequences that might be of utility, e.g., sequences that would focus enzymatic processing on particular genes or gene families. A wide spectrum of possibilities for arbitrary sequences will be apparent to those skilled in the art.

Because of nuances of syntax in the field of molecular genetics, short strands of DNA or RNA that are used to initiate enzymatically catalyzed synthetic reactions are called "primers", whereas even an identical short strand, if instead used to label and detect the sequences that they hybridize to, would be called a "probe". For this reason, throughout the description of the present invention, we have used the phrase "primer or probe". Nevertheless, this phrase is not intended to be limiting, and really refers to any nucleic acid sequence that is shorter than its template, and, for one reason or another, is used to hybridize to that template.

In several instances, we have used the phrase "prior probe interference". This term is intended to mean the ability of a primer or probe used in a first hybridization to also hybridize in a subsequent hybridization step, and thereby cause an undesired signal or synthesis reaction which is seen as a background signal.

The length of primers or probes that can be used in the various hybridizations is not limited, except that the first used primers or probes should generally be slightly shorter in length than those later used, and this length difference should be selected such that differential hybridization is possible by adjusting the stringency of the hybridization conditions.

By the term "slightly shorter", we do not mean to limit the range of differences between the lengths of the primers, except to indicate that according to the present invention, the very large differences in length such as those taught by Kawasaki [9] are not necessary. Kawasaki used hexamers in a first hybridization and 18-mers to 22-mers in a second hybridization, a difference of at least 12 base pairs; thus the second primer was three times the length of the first primer. In contrast, in the preferred embodiment described herein, first primers of 4 to 9, and preferably 5 to 7, nucleotides in length have been used, and second primers of 10 to 14 bases in, and preferably 11 to 13 bases in length, have been used. These have been combined to provide a second primer that is less than three times the length of the first primer, and preferably, to provide a second primer that is between about one and one-half and two and one-half times the length of the first primer. Of course, this should not be considered to be limiting, as it is well within the skill of the artisan to devise other suitable differential primer lengths that would be within the scope of the present invention.

In addition, the differential hybridization of probes as described herein need not be limited to that caused by differences in primer or probe length. For example, it is possible to use certain nucleic acid derivatives or analogues that hybridize less strongly than native DNA for the first step, and then use a native DNA probe or primer for a second step; in this way, differential hybridization could be exploited in accordance with the present invention, even though the length of the two primers might be the same. Alternatively, nucleic acid analogues or derivatives that bind more strongly than native DNA probes or primers could be used in the second hybridization, and native DNA could be used in the first hybridization, to again produce the differential hybridization taught by the present invention. Numerous alternative approaches are within the skill and knowledge of the artisan. For example, similar effects could also be produced by using a first primer having mostly A's and T's, and a second primer having mostly G's and C's.

It is not intended that the present invention be limited to the use of temperature to control which primers are able to hybridize to their templates. A variety of reaction conditions can affect hybridization stringency, such as temperature, ionic strength, $MgCl_2$ concentration, and solvent hydrophobicity. One, several, or all of these together might be altered in order to control which of the primers is able to hybridize to its target during the course of a particular reaction sequence. All such manipulations are within the scope of the present invention.

Where temperature is used to control hybridization, as used in the several examples hereinbelow, temperatures recited herein are not intended to be limiting, but to be examples only. Furthermore, where ranges of temperature are suggested or described, it is not intended that these be limiting, as determining suitable discreet temperatures or ranges can easily be determined by simple optimizing experiments in each particular situation.

The invention as described herein can, by those skilled in the art of molecular genetics, be easily adapted to achieve a variety of research and production objectives, some of which are illustrated by the Examples shown hereinbelow. Whenever it is desired to carry out any two or more successive manipulations that require hybridization, according to the present invention, the researcher should choose a first label or probe with a relatively low affinity for the DNA or RNA target molecule, and carry out the hybridization under conditions that strongly favor hybridization. For the next manipulation that requires hybridization, the researcher should choose a label or probe having a slightly greater length, or even having the same length, but having a distinguishably higher affinity for the DNA or RNA target than the first primer, as demonstrated by empirical experimentation. Ultimately, conditions can be developed that will allow hybridization of the second probe or label, but not allow the appreciable hybridization of the first label or probe. Similar selection should be done for subsequent steps. Although efforts to remove the previously-used primers may in some cases be unnecessary, in any event the method of the present invention will avoid background problems that can arise if such purification steps are done, but are not wholly effective.

The variations in procedure that are possible within the scope of the present invention are quite numerous, and an exhaustive description of all possibilities is neither possible nor necessary. However, in addition to the several Examples described in detail hereinbelow, there are a few other possibilities that are of interest to illustrate the range of possible adaptations of the present inventions that may be of great utility in the field of molecular genetics.

In one rather interesting embodiment of the invention, a reaction system can be constructed wherein two or three primers can be added all at once, along with the respective enzyme(s) that might utilize one or more as a primer. By simply then selecting different stringency conditions, it is possible to cycle through several stages of reaction. For example, if three primers were added, at low temperature, all primers would be used; but at a higher temperature, only two; and at the highest temperature, only one would be used. The same approach would also work for different probes for detecting the presence of particular sequences, as shown in Example 19 hereinbelow. The surprising discovery that even probes of relatively similar sizes can be differentially hybridized to target DNA by selection of different temperatures or other hybridization conditions makes such complex strategies possible.

In another interesting embodiment of the present invention, a first, short probe can be used to detect whether a particular DNA sample contains a particular sequence; this might be done by separating the DNA by agarose gel electrophoresis, flooding the gel with the labeled probe, and then detecting the label. The labeled band(s) could then be extracted, without need for particular care to remove the probe. A primer that is slightly longer than the probe could then be used to amplify the extracted DNA under stringency conditions that would disfavor the ability of the first probe to prime the PCR reaction.

According to another embodiment of the invention, selected portions of a sample of RNA can be converted to cDNA via reverse transcription using a first oligonucleotide as a primer. Then a PCR reaction is conducted using a second oligonucleotide primer at a stringency that is too severe for the first oligodeoxynucleotide to effectively function as a primer. The second oligodeoxynucleotide is selected to be fully active as a primer under such conditions. As a result, a portion of the RNA is reverse transcribed into cDNA using the first primer, and a portion of the cDNA is amplified via PCR using the second primer. Moreover, even through the first primer remains in solution during the PCR step, it does not participate in the PCR reaction because the reaction conditions are too stringent to allow it to hybridize. Unlike the method of Kawasaki [9], the differences between the sizes of the primers need not be large.

The first and second oligodeoxynucleotide primers are selected such that the first primer is unable to hybridize with a complementary template under PCR reaction conditions, while the second primer is able to hybridize. For example, when the PCR reaction is conducted using a first primer containing 7 deoxynucleotides at a temperature of 37° C. and a second primer containing 13 deoxynucleotides at temperature of 55° C. to 60° C., the first primer will not noticeably participate in the PCR reaction. A preferred PCR temperature range for the practice of the invention is 40° C. to 60° C. Preferred first oligodeoxynucleotide primers range from 6 to 8 monomers in length. Preferred second oligodeoxynucleotide primers range form 10 to 14 monomers in length.

The first nucleotide primers can be arbitrarily generated, or they can be specifically adapted to target specific RNA for reverse transcription. For example, the first primer can comprise oligo-dT to specifically target the poly(A)$^+$ tail of mRNA. Of course, all RNA with a complementary sequence will be transcribed. Likewise, the second primer can be arbitrarily generated or can be designed to target specific DNA.

There is no reason why two or more different first primers and/or two or more second primers cannot be used. Two or more first primers will create a larger cDNA library upon which PCR can be carried out. Similarly, two or more second primers can be used to target cDNA for amplification. One to three second primers is preferred.

According to the present invention, the products of the PCR reaction can be fractionated using various means known in the art. For example, the PCR products can be separated using a gel electrophoresis system and visualized using a variety of standard techniques such as autoradiography. Visualization of products is useful, for example, in comparing the PCR products of two samples of RNA to search for signs of differential gene expression. Once separated, the fragments can also be isolated, further amplified and cloned. Finally, the PCR products or the cloned DNA can be sequenced using methods known in the art such as the Sanger DNA-sequencing procedure and so forth.

Various embodiments of the invention are discussed in the Materials and Methods and Examples sections to follow. These embodiments illustrate, for example, that although previous methods, using arbitrary primers in combination with reverse transcription of RNA to examine differential gene expression (DDRT-PCR) failed either to selectively target mRNA (i.e., poly(A)$^+$ RNA) or to amplify internal and, thus, potential coding regions of the cDNA, the present invention offers an alternative strategy for performing DDRT-PCR that can target internal sequences of mRNAs. One embodiment of the protocol involves using a relatively short oligo-dT (e.g., oligo-dT$_7$) primer for the RT reaction and then performing a higher stringency PCR reaction in the presence of longer (e.g., 13-mer) oligodeoxynucleotide primers for the PCR reaction. The Examples below illustrate that under these conditions it is possible to obtain highly reproducible patterns of amplified products. Moreover, this approach avoids the relatively non-specific amplification of numerous products (noted as smearing on an autoradiograph) that are associated with using either longer poly-dT primers or poly(A)$^+$ RNA.

The embodiments illustrated below are focused primarily on using a short oligo-dT primer for the RT reaction, due to the interest in preferentially targeting poly(A)$^+$ RNA. By targeting poly(A)$^+$ RNA, it is possible to reduce spurious artifacts related to the amplification of contaminating genomic DNA or ribosomal RNA. In differential display analysis this is particularly important because differential levels of contamination between samples will result in amplified products that appear to be differentially expressed. Nonetheless, the below Examples also illustrate that, when the RNA is DNase treated, it is also possible to use other short primers such as arbitrary hexamers in the RT reaction without adversely affecting the PCR results. Moreover, this approach would also be suitable for targeting specific gene sequences (e.g., gene family specific) with short selected primer(s) in the RT reaction that would not participate in a second higher stringency PCR reaction.

Other Examples of the invention discussed below illustrate the utility of a higher hybridization temperature in the PCR reaction than in the RT reaction. Previous protocols using arbitrary primers used lower hybridization temperatures (e.g., 40° C.) to enhance the likelihood of amplifying many target cDNAs. However, in order to discourage PCR amplification involving the short RT primers, in the present invention, the hybridization temperature is increased during PCR to increase the stringency of the hybridization reaction. The Examples illustrated below show that, surprisingly, it is possible to increase the hybridization temperature up to 60° C. in the presence of 13 or 14-mers and still amplify 50–75 cDNAs. Moreover, it is shown below that the results are not markedly different when the Taq polymerase is added after the initial denaturing step (i.e., "hot start"), indicating that an initial low stringency hybridization step is not essential. Interestingly, the profile of cDNAs (i.e., the RNA fingerprint) is shown to be affected by increasing hybridization temperature, suggesting that greater specificity may be gained with higher stringency conditions. This improved specificity will likely facilitate targeting of specific-mRNAs which have been a problem with previous differential display protocols [1]. It is also seen below that at the higher hybridization temperature, there is less background signal, indicating that there is less non-specific amplification. This result should enhance the ability to adapt this method to automated image analysis.

Still other Examples illustrated below relate to the optimization of PCR primer lengths and the number of different PCR primers for a given set of conditions. 8–14-mers were tested and it was found that for hybridization temperatures $\geq 55°$ C., 13-mers were ideal for PCR. The shorter primers (i.e., 8–10-mers) failed to generate enough PCR products at such temperatures, presumably because they melted off. Although the ideal primer length will depend upon various factors such as the stringency of the reaction conditions, 13-mers with approximately 60% G+C content were found to be an excellent choice.

The Examples below also concern the effect of different numbers of PCR primers on the PCR reaction and showed that 2 primers generated the most products under the conditions tested. Adding 3 or more primers was seen to reduce the number of products. Because 2 primers, unlike a single primer, enables targeting specific cDNAs and also enables visualization of many products, this appears to be a preferred choice for differential display analysis.

The foregoing and following descriptions of the invention and the various embodiments are not intended to be limiting, as those skilled in the art of molecular genetics can easily formulate further embodiments that are within the scope of the present invention.

MATERIALS AND METHODS

1. Isolation of RNA

A number of methods have been described that allow the isolation RNA from cells or tissues. These can be found in any molecular biology manual or are available as a kit from numerous commercial vendors.

In the Examples to follow, mIMCD-3 cells (Rauchman) were grown to confluence on plastic dishes in DMEM/F12 (1:1) supplemented with 1% fetal bovine serum. Cells were washed twice with PBS and total RNA was isolated using the RNAzol B method (Tel-Test, Inc). Poly(A)$^+$ RNA was isolated by using oligotex-dT (Qiagen).

2. DNase treatment of RNA

Various methods are available for eliminating DNA from a given RNA sample, and for limiting enzymatic degradation of the RNA. In the Examples to follow, to eliminate genomic DNA contamination, 30 $\mu$g of total or poly(A)$^+$ RNA was incubated with 50 U RNase inhibitor (Pharmacia), 50 mM KCl, 10 mM Tris-HCl (pH 8.3), 1.5 mM MgCl$_2$, and 10 U DNase (GIBCO/BRL). This 50 $\mu$l reaction mixture was incubated for 30 min at 37° C. and transferred to ice. The sample was subjected to a phenol/chloroform extraction procedure, precipitated with ethanol, and re-suspended in 15 μl DEPC-treated water. RNA was quantitated spectrophotometrically.

3. Reverse transcription

Using isolated total RNA, a standard reverse transcription reaction can be run using any one of a number of commercially available reverse transcriptase enzymes (e.g., MMLV RT, Superscript RT) in order to synthesize single stranded cDNA. Unlike previous differential display methods, our method requires the use of a relatively short oligodeoxynucleotide primer, ranging, for example, from 4-mers to 9-mers. Previous differential display methods used either "anchored" oligo-dT primers generally consisting of $dT_{12}$ plus two additional 3' deoxynucleotides [3] or a oligonucleotide primer which contained no oligo-dT sequence at all [5].

In the experiments described in the Examples below, reverse transcription (RT) was conducted as follows: A 10 μl reaction mixture containing 2 μg RNA, 10 U RNase inhibitor, and 20 mM dithiothreitol (DTT) was incubated at 65° C. for 10 min and put on ice. To this reaction mixture was added 50 mM KCl 10 mM Tris-HCl (pH 8.3), 5 mM $MgCl_2$, 20–250 μM dNTPs (see below; Pharmacia), 2.5 μM of the appropriate oligo-dT primer, and 200 U MMLV reverse transcriptase (GIBCO/BRL). The sample was incubated for 1 hour at 37° C., heated to 99° C. for 5 minutes and then chilled on ice for 5 minutes. The resulting cDNA was then stored at −20° C.

4. Polymerase chain reaction (PCR)

The single stranded cDNA product described above, which still contains the primer from the RT reaction, can now be mixed with additional primers and any other appropriate ingredients to perform a PCR reaction. Alternatively, these primers can be added to the initial reaction mixture prior to reverse transcription. These ingredients should include a thermostable DNA polymerase (e.g., Taq polymerase), dNTPs, and appropriate salts and buffers, if not already present. To the reaction mixture is added a suitable label (e.g., $^{35}$S-DATP, fluorescently labeled primers), enabling subsequent visualization and analysis of the amplified products. In the present invention, the length of the primers and the stringency of primer hybridization in the PCR reaction (e.g., temperature, $MgCl_2$, concentration, ionic strength, etc.) are very important. It is important that the stringency be sufficiently high such that the primer used in the RT reaction does not act as a substantially effective primer in the PCR reaction. The degree of stringency needed for effective reaction will generally depend on the length of the PCR primers, and ability to prevent priming of the PCR reaction by the RT primer will generally depend on the RT primer's length.

In our experiments, we have increased stringency by increasing the hybridization temperature of the PCR reaction as compared to the RT reaction. The PCR primers should be of sufficient length and be comprised of an appropriate mixture of all four deoxyribonucleotides to ensure that the primer hybridizes relatively specifically at the hybridization temperature of the PCR reaction (e.g., 50° C.). The selection of primer length, number of primers and hybridization stringency (i.e., temperature, ionic strength, and $MgCl_2$ concentration) is based on a desire to amplify reproducibly a sub-set of cDNAs, preferably approximately 50–300. The number of amplified products desired depends on the resolving power of the electrophoresis system. Moreover, the primers and hybridization conditions must be chosen to enhance the amplification of specific products (noted as stronger intensity and reproducible bands) and reduce the amplification of non-specific products (noted as a background smear on the gel).

If the hybridization stringency is too high, no amplification will occur; if it is too low, significant PCR amplification from the RT primer will occur. Our experience has shown that when the RT primer can act as a primer in the PCR reaction this leads to amplification of numerous products of all sizes resulting in a background smear in the lanes, particularly near the top of the gel where larger PCR products migrate. These "background" products are non-specific and obscure and complicate the analysis and isolation of the specific products; they are therefore best to be avoided by careful optimization of the stringency requirement.

In the Examples to follow, to 1 μl of the cDNA was added 1.25 mM $MgCl_2$, 50 mM KCl 10 mM Tris-HCl (pH 8.3), 2.5 μM of the 3' primer used in the RT reaction, 0.5 μM of the arbitrary primer(s) (8–13-mers), 5 μCi (~368 nM) [$^{35}$S]-DATP (DuPont/NEN), and 0.3 U Taq DNA polymerase. The total reaction volume was 10 μl. Using a thermal cycler (MJ Research) PCR was performed as follows: 95° C. for 1 minute, then 40 cycles of 94° C. for 15 seconds, the appropriate hybridization temperature (40° C.–65° C.) for 45 seconds, and 72° C. for 30 seconds, and then a final extension period at 72° C. for 10 minutes. After the PCR reaction the samples were chilled to 4° C. and 10 μl of PCR stop solution containing 10M EDTA, 0.03% bromophenol blue, 0.03% xylene cyanol, and 95% formamide as added. The samples were stored at −20° C. until they were loaded on the gel.

5. Gel electrophoresis

The PCR products can be run on a denaturing or non-denaturing polyacrylamide gel electrophoresis system to resolve the individual products. Bauer and coworkers [1] have described the advantages of non-denaturing gels. After electrophoretic separation, the PCR products are then visualized using any of a variety of standard techniques appropriate for a given label. For example, when using $^{35}$S-dATP, the gel can be exposed to X-ray film for autoradiography. Or, silver staining could be used to visualize bands, thus avoiding the need for radiolabeling.

Alternatively, as described by Bauer and coworkers, an automated DNA sequencing system (e.g., ABI) can be used to visualize and potentially analyze the bands. The intensities of the bands are compared in order to distinguish those products that are relatively more or less abundant in each sample. Appropriate size standards can be added to improve identification of individual cDNAs when analyzing multiple RNA samples.

In the Examples to follow, denaturing 6% polyacrylamide-urea gels were prepared using Sequagel (National Diagnostics). Samples (15 μl) were loaded and run at 1500 V for 2–3 hours until the bromophenol blue dye ran off the gel. The gel was transferred to filter paper, dried, and exposed to film (Reflection NEF495, DuPont) for 6 hours to 3 days.

6. Excision of DNA fragments and PCR re-amplification

In the Examples to follow, individual DNA fragments observed on the autoradiographs were excised from the gels with a razor blade and incubated overnight at room temperature in a 0.5 ml solution of 0.5M ammonium acetate, 1 mM EDTA (pH 8.0). The cDNA fragments were ethanol precipitated, washed, lyophilized, and reconstituted in 10 μl water. To the cDNA was added 2 mM $MgCl_2$, 50 mM KCl, 10 mM Tris-HCl (pH 8.3), 20 μM dNTPs, 1.25 μM primers, and 2 U Taq DNA polymerase. The PCR amplification thermal cycling protocol was identical to that describe above with the hybridization temperature based on that used in the initial DDRT-PCR reaction.

7. Cloning cDNAs fragments

In the Examples to follow, re-amplified cDNA products were separated on a 2% agarose gel and isolated using a DNA gel extraction kit (QIAEX). They were then blunt end ligated into pBluescript SK+. Briefly, in a total volume of 25 µl, the cDNA product was mixed with 100 µM dNTPs, 1.25 µg bovine serum albumin, 1 U T4 DNA polymerase, 1×T4 DNA polymerase buffer, and incubated at room temperature for 30 minutes. After heating the reaction mixture to 75° C. for 10 min to inactivate the T4 DNA polymerase, the reaction mixture was chilled on ice. Then to this was added 1 µl water, 3 µl ATP (10 mM stock), and 1 µl T4 polynucleotide kinase (10 U/µl ), and the reaction mixture was then incubated for 1 hour at 37° C. The reaction was heated to 65° C. for 20 minutes and the cDNA was isolated by phenol/chloroform extraction and ethanol precipitation. The ligation reaction (10 µl) contained the 0.05 pmol cDNA, 1×ligase buffer, 0.01 pmol pBluescript SK+ vector, and 200 U T4 ligase. The ligation mixture was incubated at 16° C. overnight, heated to 65° C. for ten minutes, and chilled on ice. Competent bacteria were transformed and plated on IPTG and XGal plates. Individual clones were purified, plasmid DNA was isolated (Qiagen), and the DNA was sequenced at the Howard Hughes Biopolymers Research Facility at Harvard Medical School. DNA and deduced amino acid sequence comparisons were made to the Genbank DNA database, the Genbank Combined Protein Database (includes the PIR, Translated Genbank, and Swissprot databases) and the Kabat, and transcription factor protein databases using the Autosearch program at the Molecular Biology Computer Research Resources facility at Dana Farber/Boston University.

8. Oligonucleotide primers

In the Examples to follow, synthetic oligonucleotide primers were purchased from Oligos Etc (Portland, Oreg.) and were prepared as 200 µM stock solutions in water. Such primers are readily available from a variety of other sources, or can be synthesized by using standard DNA synthesizing reactions and equipment. oligonucleotides used in the following examples were stored at 4° C. until use. The oligos that were used for the reverse transcription reaction included: oligo-dT$_6$, oligo-dT$_7$, oligo-dT$_8$, and arbitrary hexamers. The PCR reaction was performed with combinations of the following arbitrary primers (5' TO 3'): K10 (SEQ ID NO:1), GCCACCATGG; K11 (SEQ ID NO:2), TGCCACCATGG; K12 (SEQ ID NO:3), ATGCCACCATGG; K13 (SEQ ID NO:4), GATGCCACCATGG; R10 (SEQ ID NO:5), GTCTGGTTCT; R11 (SEQ ID NO:6), CGTCTGGTTCT; R12 (SEQ ID NO:7), GCGTCTGGTTCT; R13 (SEQ ID NO:8), TGCGTCTGGTTCT; CTG1TGCGTCTGGTTCT; A13 (SEQ ID NO:9), CGAATCCGAGTGA; B13 (SEQ ID NO:10), TGCTTCAGCACTG; C13 (SEQ ID NO:11), GACGGACAGCTTC; and D13 (SEQ ID NO:12), AGCGATACGAGGC. Note that the K (SEQ ID NO:1–5) series and R (SEQ ID NO:6–10) series of primers are 10–14-mers in which bases are added sequentially to the 5' end; in each series the 10 terminal bases are identical in all 5 primers.

EXAMPLES

Example 1

Use of short poly-dT primers and slightly longer PCR primers

In order to determine the effects of primer length on the method according to the present invention, total RNA was reverse transcribed in the presence of oligo-dT$_6$, oligo-dT$_7$ and oligo-dT$_8$. Samples of the cDNAs produced by each of these reactions were then used as templates for PCR, using arbitrary primers of 10, 11, 12, or 13 bases in length.

The results are shown in the autoradiograph of FIG. 1. The autoradiograph shows that performing the DDRT-PCR reaction under conditions that would preferentially use poly (A)$^+$ RNA as the template for the RT reaction but not target the poly(A)$^+$ tail in the PCR reaction gave remarkably low background levels. When oligo-dT$_6$, oligo-dT$_7$, or oligo-dT$_8$ was used for the RT reaction and two primers ranging in size from 10–13-mer were used for the PCR reaction, specific PCR products could be visualized. In this example, the PCR reaction was performed at 40° C. with pairs of 10–13-mer primers, and a smear was not observed when the oligo-dT$_6$ or oligo-dT$_7$ primers were used. However, when the oligo-dT$_8$ primer was used for the RT reaction, a minor smear was visible in the upper portion of the lanes, suggesting that the oligo-dT$_8$ primer was to some extent being used to prime the PCR reaction as well. Thus, it appears that, under the conditions used, either the oligo-dT$_6$ or oligo-dT$_7$ primer in combination with longer arbitrary primers (10 to 13-mers) was preferred for the DDRT-PCR reaction.

In this Example, there is also additional information available regarding the utility and specificity of the different primer lengths in the PCR reaction. One aim of DDRT-PCR is to amplify multiple cDNAs, so that many can be compared at once, thus minimizing the number of analyses needed to effectively screen the entire genome. In this experiment, 50–80 individual cDNAs could be clearly distinguished under every condition, indicating that the general approach is valid. The number of distinct bands was relatively constant in all lanes with the possible exception of those PCR reactions performed with 10-mer primers, in which case there were slightly fewer bands. In terms of the profile of cDNAs, some cDNAs were consistently amplified under all experimental conditions and can be seen in each set of lanes as slightly increasing sized products related to the increased length of the primers. However, there were a number of cDNAs that were not amplified under all conditions, particularly some of those observed in the first two lanes using 10 and 11-mers in combination with the oligo-dT$_6$. Of particular note was the fact that the profile of cDNAs was nearly identical when the larger primers (12 and 13-mers) were used in combination with the oligo-dT$_7$ or oligo-dT$_8$ primed RT reaction. Overall, it appears from this experiment that using oligo-dT$_7$ to prime the RT reaction enables one to preferentially select poly(A)$^+$ RNA without adversely affecting the PCR reaction.

Figure 2:
FIG. 2 is an autoradiograph showing the comparatively poor results obtained when oligo-dT-primed Poly(A)+ RNA is used as a template for DDRT-PCR using the prior art method of Liang and Pardee (3)

The remarkable results obtained in this and similar experiments can best be appreciated by comparison with the results obtained when mRNA was instead first purified on an oligo-dT column, and was then used to prime the reverse transcription reaction; such results are shown for three different samples in FIG. 2. Few specific bands were observed and the results generally showed a smear of products, presumably because oligo-dT leached from the column and contaminated the PCR reaction mixture, and because its length was not limited, it was used as a primer by the Taq polymerase. A similar result was obtained previously by Liang and coworkers [2]. Because a denaturing gel was used here, each product is represented by up to 4 bands, which can be seen individually in the bottom part of the autoradiograph.

Example 2

Effect of increasing hybridization temperature

Having identified suitable primer lengths by the optimization experiment of Example 1, the stringency of the PCR conditions was then optimized by altering the PCR hybridization temperature in the DDRT-PCR reaction. Total RNA was reverse transcribed using oligo-dT$_7$ as a primer. Three primers with lengths of 12-mer, 13 mer and 14-mer were then used in the PCR reaction with different primer hybridization temperatures of 40° C., 45° C., 50° C., 60° C. and 65° C.

Figure 3:
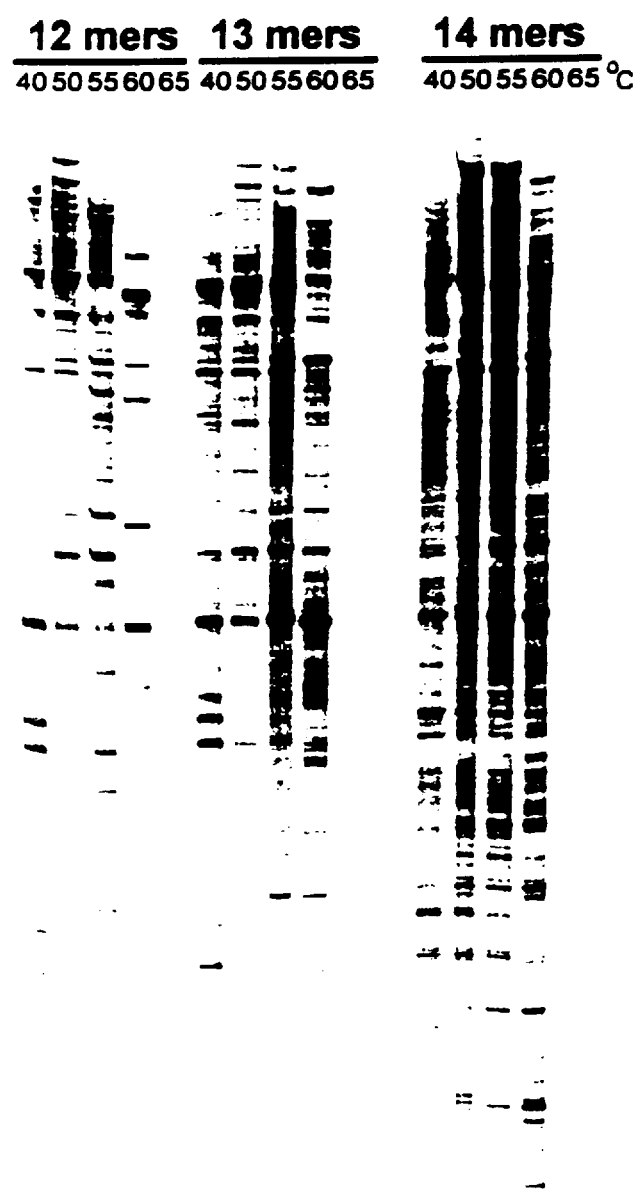
FIG. 3 is an autoradiograph showing the effects of altering the PCR hybridization temperature in the DDRT-PCR reaction according to the method of the present invention.

The results of this experiment are shown in FIG. 3. With all primers used, there were no PCR products detected at 65° C., presumably because this temperature is sufficiently high to melt the nucleotide primers off the cDNA template. The 12 nucleotide primers were less effective than either the 13 or 14-mer primers in terms of the number of distinct products detected. In fact, when using the 12-mer primers there were many fewer products observed when the temperature was increased to 60° C. Though not shown, shorter primers (8–11-mers) were even less effective at the higher temperatures. Both the 13 mers and 14-mers were effective in the PCR reaction at all temperatures from 40° to 60° C. Typically, however, the 14-mers tended to generate a darker background that made it more difficult to discern individual bands, whereas the 13-mers appeared to be effective at all temperatures.

Of particular interest was the effect of increasing hybridization temperature on the profile of cDNAs that were observed. For any particular set of primers, increasing the temperature caused subtle but significant changes in the profile of amplified products. Some bands were present at all temperatures whereas others were predominantly evident at either lower or higher. Of particular note was the fact that at 60° C. the profile of cDNAs was distinctly different from that seen at 40°–50° C.

Although any of several conditions seen in FIG. 3 seemed to be suitable for DDRT-PCR, it appears that for the particular conditions and RNA samples used here, the optimal conditions would be to use 13-mer primers at 55° to 60° C. Moreover, because the higher temperature likely requires greater identity between the cDNA template sequence and the primer sequence, these higher temperatures would be preferable for targeting specific sequences.

Example 3
Analysis of RNA samples with different PCR primers

In order to illustrate the general utility of the present invention with various primers, DDRT-PCR was performed according to the present invention using three different RNA samples (1,2 and 3) and four completely different PCR primer combinations (A, B, C, and D) at 55° C. The three samples of total RNA were reverse transcribed in the presence of oligo-dT$_7$ primer and PCR amplified using different sets of two 13-mer primers. The primer hybridization temperature was 55° C.

Figure 4:
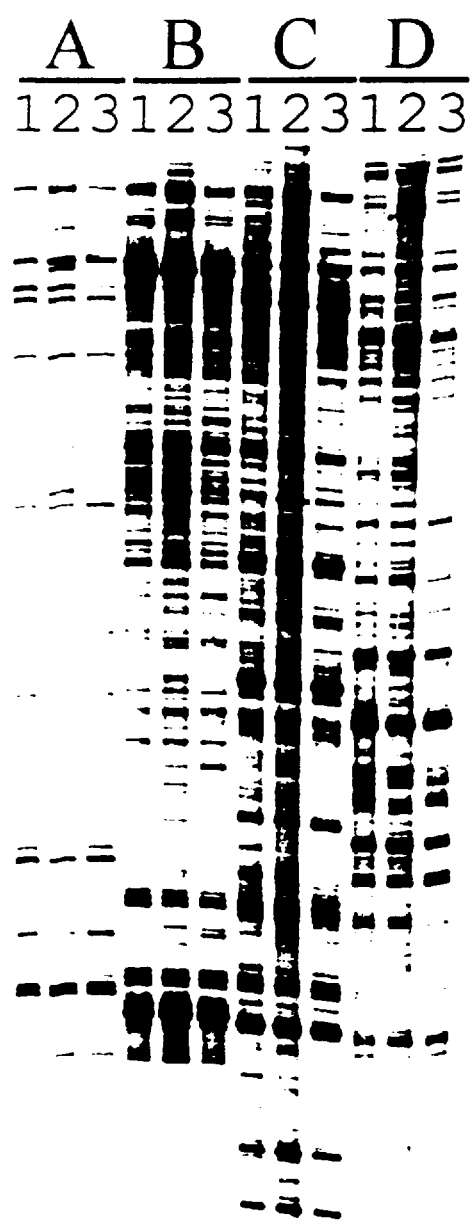
FIG. 4 is an autoradiograph showing the results of DDRT-PCR according to the method of the present invention, illustrating the utility of the method for routine analysis of differential gene expression.

The results of this experiment are shown in FIG. 4. It is evident that in every case, 50–80 PCR products were amplified. Moreover, it is possible to distinguish products that are differentially modulated. Thus, these conditions are suitable for routine analysis of differential gene expression.

Example 4
"Hot start" PCR

In the protocol used in the prior examples, the Taq polymerase was added to the reaction mixture before the initial heating to melt the strands apart. Thus, PCR was performed under conditions that would allow first strand synthesis to begin at a low temperature during the initial heating of the reaction to 94° C. It was therefore important to examine whether adding the Taq polymerase either before or after the initial denaturing step had an effect on the PCR products which were generated.

In this experiment, using the same lot of cDNA which was reverse transcribed with oligo-dT$_7$, a PCR reaction was performed using two 13-mer primers. In one case, the Taq polymerase was added before the initial melting, while in the other case, the polymerase was added only after heating to 94° C. to cause the initial melt, giving the enzyme a "hot start".

Figure 5:
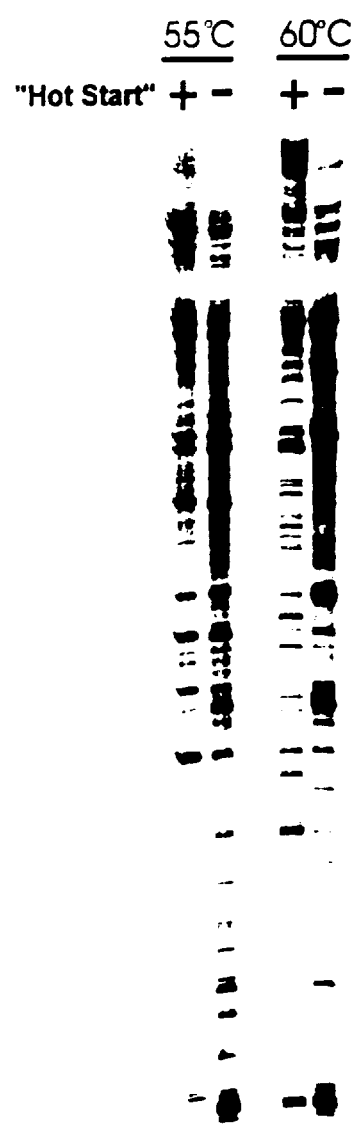
FIG. 5 is an autoradiograph showing the effect of a "hot start" on DDRT-PCR, that is, the effects of adding Taq polymerase after the initial denaturing step rather than before.

The results are shown in FIG. 5. The autoradiograph shows that at both hybridization temperatures, the number of cDNA products was not greatly affected by the "hot start" procedure. However, there were some differences in the products that were observed, particularly at 60° C.

Example 5
Arbitrary hexamer priming of the RT reaction

Although there are certain benefits from using oligo-dT to prime the reverse transcriptase reaction, it seemed likely that arbitrary, short primers could also be used to prime the reverse transcription reaction.

In this experiment, arbitrary hexamers (having six arbitrarily selected bases, designated "RH") and oligo-dT$_7$ (having seven "T"s, designated "T7" in FIG. 6) were alternatively used as primers in the RT reaction, followed by PCR using a arbitrary 13-mer as the primer at 55° C. and 60° C.

Figure 6:
FIG. 6 is an autoradiograph comparing the use of arbitrary hexamers (designated "RH") and oligo-dT$_7$ (designated "T7") as primers in the reverse transcriptase reaction, followed by PCR using arbitrarily selected primer sequences.

The results are shown in FIG. 6. In general, the amplified cDNA products were highly similar using either RT primer. At two different hybridization temperatures, the arbitrary hexamer primed DDRT-PCR reaction yielded strikingly similar results to those observed when the polydT$_7$ primer was used. The number of bands and amount of non-specific background signal were comparable. Moreover, the profile of PCR products observed with these different RT primers was similar but not identical. This suggests that the 13-mers are not preferentially targeting the most 3' end of the cDNA. Moreover, there was a general tendency for abundant products observed with the arbitrary hexamer primers to also be relatively abundant when using the polydT$_7$ primer. Thus it appears that arbitrary primers can be used to prime the RT reaction rather than oligo-dT, with comparable or at least equally useful results.

Example 6
Effect of number of primers

To consider the effect of altering the number of primers in the PCR reaction on the number and intensity of the amplified products, following reverse transcription, the PCR reaction was conducted using 1, 2, 3, 4, 5 and 6 different 13-mer primers at a primer hybridization temperature of 55° C.

Figure 7:
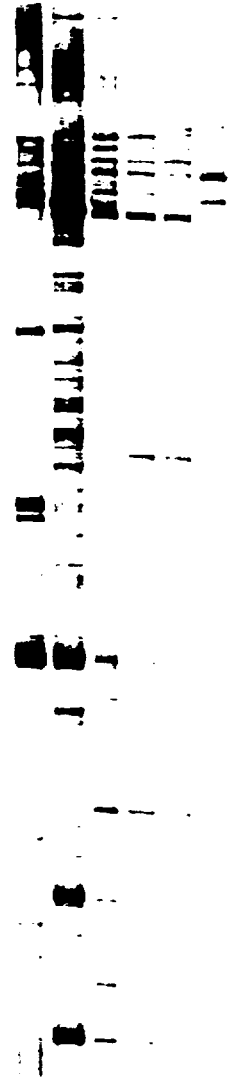
FIG. 7 is an autoradiograph showing the effects that altering the number of primers used in the PCR reaction has on the number and intensity of the amplified products.

The results are shown in FIG. 7. The primers used were: in lane 1, D13; in lane 2, D13+C13; in lane 3, D13+C13+B13; in lane 4, D13+C13+B13+A13; in lane 5, D13+C13+B13+A13+R13; in lane 6, D13+C13+B13+A13+R13+K13. The autoradiogram shows that a single primer, as used previously [5, 6] generated a few very intense bands. Two primers yielded significantly more products, but addition of even more primers reduced the number of PCR products observed. The same results were also obtained with other sets of primers. Thus, two primers appears to be a better choice than using three or more. However, given the intensity of the bands seen with the single primer, in some cases this is likely to be a reasonable choice.

Example 7
Re-amplification of individual bands

Figure 8:
FIG. 8 is an autoradiograph showing the products of re-amplifying several individual cDNA products that were excised and extracted from DDRT-PCR polyacrylamide gels.

In order to demonstrate that the PCR products that were generated by the oligo-dT$_7$ primed DDRT-PCR reaction were amplified by the 13-mer primers and not by the oligo-dT$_7$, after performing a DDRT-PCR reaction, eight individual cDNA fragments were cut from the gel, eluted and re-amplified at 55° C. with either all three primers or just the two 13-mers (K13 and R13). Seven individual cDNAs were then isolated and re-amplified using either all three primers (lane 1) or only K13 and R13 (lane 2). The results are shown in FIG. 8. The autoradiogram shows that in the absence of the oligo-dT$_7$, all of the products were still amplified. Thus, using this method it appears that the 13-mers are the preferred primers in the higher stringency PCR reaction. Moreover, since the two 13-mer primers alone were able to re-amplify all seven cDNAs, this experiment shows that essentially none of the cDNAs were primed by the oligo-dT$_7$ primer during re-amplification. The RT primer used in the method of the present invention does not participate in PCR amplification.

Example 8
DNA sequence analysis

To ascertain whether this method could amplify internal cDNA fragments, four cDNAs were re-amplified, cloned, sequenced, and compared to the Genbank DNA database, the Genbank Combined Protein Database (includes the PIR, Translated Genbank, and Swissprot databases) and the Kabat, and transcription factor protein databases. Based on this analysis all appeared to be derived from internal DNA sequences. One cDNA fragment was identical to the murine AE1, Cl/HCO$_3$ exchanger cDNA [10] but represented a non-coding 3' region of the cDNA (several hundred bases upstream of the poly-A tail). Based on a comparison of the open reading frames to the various databases, the other three cDNAs appeared to contain protein coding sequence. In each case, a single open reading frame was highly similar to a protein in one or more of the databases searched. One cDNA was homologous to a recently identified human transcription factor, a match that was apparent at both the DNA and amino acid sequence levels. More significantly, however, the other two cDNAs showed striking similarity to yeast and *C. elegans* deduced proteins, but not their corresponding cDNAs. Thus, we could rapidly define a putative function for these cDNAs based on finding homologous proteins from highly divergent species, an inference that is rarely feasible when only the 3' untranslated regions are studied, as is the case in the prior art method of Liang and Pardee [3].

Example 9
Optimization of dNTP concentration

When we initially began using the protocol described by Liang and Pardee [3] we noted that there could be considerable variability in the results. We examined a number of potential variables and determined that the major problem was variations in the activity of different lots of MMLV reverse transcriptase enzyme. To overcome this problem it was necessary to optimize the concentration of dNTPs used in the reaction.

Figure 9:
FIG. 9 is an autoradiograph showing the effect of changing the concentration of the various dNTPs on the products of the RT-PCR reaction.

To optimize these concentrations, dNTPs were added to the reverse transcriptase reaction at concentrations ranging from 20 to 240 $\mu$M. No new dNTPs were added for the PCR reaction. The results are shown in FIG. 9. At low concentrations, few or no bands are seen. As the DNTP concentration increases, more products are seen, and their average size increases. At the highest concentrations shown in the Figure, a significant background appears; a smear towards the top of the autoradiograph is seen.

Though not shown, very high dNTP concentrations led to decreased signal intensities, presumably by diluting the radioactive dATP. These data indicate that it is very important to determine the optimal dNTP concentration to be used with each lot of reverse transcriptase. In this example we chose to use 100 $\mu$M dNTPs for this lot of MMLV.

It should be emphasized that in our DDRT-PCR protocol dNTPs were added to the reverse transcription reaction only. We did not add additional dNTP to the PCR reaction, so the PCR reaction used only those dNTPS that were carried over from the reverse transcription reaction.

Example 10
Simultaneous Multiple cDNA library screen

A partial amino acid sequence has been deduced for a protein of interest, and this sequence is deciphered using the genetic code to determine what probes should be synthesized for cDNA screening. However, it is recognized that using such probes to screen cDNA libraries can be problematic. Sometimes it turns out that the probes used will hybridize to far too many cDNAs; sometimes it turns out that they will not hybridize to any at all; and sometimes, as desired, only a few cDNAs will hybridize. Unfortunately, it is generally necessary to screen a large percentage of the library before it becomes apparent which is the case. In the first or second instances, it is necessary to change the stringency of the hybridization, and then begin screening all over again.

To overcome this problem, three different sets of probes are constructed. One set of probes are the longest possible, based on the known protein sequence. A second set are of intermediate length, and a third set are relatively short. All three sets of probes are then mixed together, and the mixture is end-labeled with P$^{32}$. These are then used as probes to screen a cDNA library. Briefly, library bacteria are plated out thinly on petri dishes, and incubated until each cell has formed a colony. The DNA in the colonies present on each dish are then blotted onto nitrocellulose filters using standard methods, and the mixed probe is added in a low-stringency hybridization buffer, e.g., one containing a low salt concentration. All three probes will bind under these conditions. The filters are then washed, and then are covered with plastic wrap and exposed to X-ray film to detect which colonies contained cDNA that hybridized to one or more of the probes. Then, the filters are washed again, this time in intermediate-stringency buffer. They are then covered and re-exposed to an X-ray film, to determine which colonies contained cDNA that hybridized to one of the two longer probes. Lastly, the filters are washed again, this time in a high-stringency buffer. They are then covered and re-exposed to an X-ray film, to determine which colonies contained cDNA that hybridized to the longest probes. After all three films are developed, by comparing presence or absence of dark spots on each film, it is determined which colonies hybridized to which of the three probes. As needed, densitometry scans are made on individual spots to determine whether a given spot represents labeling by only one or by more than one probe.

The final result is that three library screenings have been carried out at once. This not only allows for optimum screening efficiency in a single pass, but also allows for the potential detection of cDNAs that bind the probe at lower stringency, which may encode proteins that are structurally or functionally related to the protein of interest.

REFERENCES

1. Bauer, D., H. Muller, J. Reich, H. Reidel, V. Ahrenkiel, P. Warthoe, and M. Strauss. "Identification of differentially expressed mRNA species by an improved technique (DDRT-PCR)." *Nucl. Acids Res.* 21: 4272–4280, 1993.

2. Liang, P., L. Averboukh, K. Keyomarsi, R. Sager, and A. B. Pardee. "Differential display and cloning of messenger RNAs from human breast cancer versus mammary epithelial cells." *Cancer Res.* 52: 6966–6968, 1992.
3. Liang, P., and A. B. Pardee. "Differential display of eukaryotic messenger RNA by means of the polymerase chain reaction." *Science* 257: 967–971, 1992.
4. Sager, R., A. Anisowicz, M. Neveu, P. Liang, and G. Sotiropoulou. "Identification by differential display of alpha 6 integrin as a candidate tumor suppressor gene-."*FASEB J.* 7: 964–970, 1993.
5. Welsh, J., K. Chada, S. S. Dalal, R. Cheng, D. Ralph, and M. McClelland. "Arbitrarily primed PCR fingerprinting of RNA." *Nucl. Acids Res.* 20: 4965–4970, 1992.
6. Welsh, J., and M. McClelland. "Fingerprinting genomes using PCR with arbitrary primers." *Nucl. Acids Res.* 18: 7213–7218, 1990.
7. Barnes, W. M. "PCR Amplification of up to 35-kb DNA with high fidelity and high yield from λ bacteriophage templates." *Proc. Natl. Acad. Sci. USA* 91: 2216–2220, 1994.
8. Zou, Z., A. Anisowicz, M. J. C. Hendrix, A. Thor, M. Neven, S. Sheng, K. Rafidi, E. Seftor and R. Jager. "Maspin, a Serpin with Tumor-Suppressing Activity in Mammary Epithelial Cells." *Science* 263: 526–529, 1994.
9. Kawasaki, E. S. "Amplification of RNA." in: *PCR Protocols: a Guide to Methods and Applications*, p. 21–27, Academic Press, 1990.
10. Kopito, R. R. and H. F. Lodish. "Primary Structure and Transmembrane Orientation of the Murine Anion Exchange Protein." *Nature* 316: 234–238, 1985.

---

We claim:

1. A method of minimizing prior probe interference in processes using successive nucleic acid hybridization steps, comprising the steps of:

(A) hybridizing, in the first nucleic acid hybridization step of said processes, a first probe or primer to at least one complementary template under stringency conditions that are sufficiently low to allow hybridization to take place, and (B) in each successive nucleic acid hybridization step of said processes hybridizing each successive probe or primer to its complementary template under conditions of successively higher stringency, such that the hybridization of the successive probe or primer is favored, while the hybridization of prior-used probes or primers is disfavored;

wherein the length of each successive probe or primer is longer than the length of the immediately prior-used probe or primer, but less than three times of said length and whereby prior-probe interference is minimized.

2. The method of claim 1 wherein each successive probe or primer is less than about 12 nucleotides longer than the immediately prior-used probe or primer.

3. The method of claim 1 wherein at least one of said first and successive primers is acted upon by a polynucleotide synthetase prior to the change in conditions that disfavors its hybridization to its complementary template.

4. The method of claim 3 wherein the first primer is selected from the group of oligo-dT and arbitrary polynucleotides, and the polynucleotide synthetase acting thereon is reverse transcriptase.

5. The method of claim 3 wherein at least one of said first and successive primers is used to initiate enzymatic amplification of all or part of the template.

6. The method of claim 5 wherein said amplification is the polymerase chain reaction.

7. The method of claim 1 wherein the hybridization of at least one of said first and successive probes to its complementary template is detected prior to the change in conditions that disfavors its hybridization to said template.

8. The method of claim 1 wherein a plurality of probes to be used in said successive hybridizations are added to the initial reaction mixture.

9. The method of claim 1 wherein said conditions of low stringency and successively higher stringency differ in one or more parameters selected from the group of temperature, ionic strength, $MgCl_2$ concentration, and solvent hydrophobicity.

10. A method for differential display reverse transcription-amplification, comprising the steps of:

(1) reverse transcribing the mRNA in a RNA sample to produce cDNA by using one or more polynucleotide primers to prime the enzyme reverse transcriptase;

(2) adding one or more additional primers that are longer than the length of the polynucleotide primers of step (1), but less than three times of said length and using said additional primers to amplify segments of the template cDNA produced in step (1) under conditions which favor hybridization of the longer primers to the template cDNA, but disfavor hybridization between the shorter primers and said template cDNA; and (3) differentially displaying the products of the reverse transcription-amplification.

11. The method of claim 10 wherein said polynucleotide primer is selected from the group of oligo-dT and arbitrary polynucleotides.

12. The method of claim 11 wherein said polynucleotide primer is more than 4 bases in length.

13. The method of claim 10 wherein said amplification is carried out using the polymerase chain reaction (PCR).

14. The method of claim 10 wherein said longer primers are more than 10 bases in length.

15. The method of claim 10, wherein all method steps are separately performed on cellular RNA samples from a plurality of sources, and the amplified sequences thereby obtained from each sample are compared to determine whether one or more amplified sequences are augmented or suppressed relative to the amplified sequences of one or more other sources.

16. The method of claim 15 wherein the amplified DNA sequences are separated according to size, and the sizes of said sequences obtained using RNA samples from normal and diseased individuals are compared to detect whether one or more amplified sequences are relatively augmented or suppressed.

17. The method of claim 16 wherein the reactions and size separations are carried out substantially by automated machines.

\* \* \* \* \*

UNITED STATES PATENT AND TRADEMARK OFFICE
CERTIFICATE OF CORRECTION

PATENT NO. : 5,773,213
DATED : 30 June 1998
INVENTOR(S) : Steven R. GULLANS et al.

It is certified that error appears in the above-identified patent and that said Letters Patent is hereby corrected as shown below:

| Column | Line | |
|--------|------|---|
| 2 | 30 | Change "Taq" to --*Taq*--. |
| 11 | 11 | Change "Taq" to --*Taq*--. |
| 16 | 8 | Change "Taq" to --*Taq*--. |
| 17 | 37 | Change "Taq" to --*Taq*--. |
| 18 | 17 | After "KCl" insert --,--. |
| 18 | 20 | Change "Taq" to --*Taq*--. |
| 18 | 67 | Change "Taq" to --*Taq*--. |
| 19 | 53 | Delete "CTG1TGCGTCTGGTTCT;" |

UNITED STATES PATENT AND TRADEMARK OFFICE
CERTIFICATE OF CORRECTION

PATENT NO. : 5,773,213
DATED : 30 June 1998
INVENTOR(S) : Steven R. GULLANS et al.

It is certified that error appears in the above-identified patent and that said Letters Patent is hereby corrected as shown below:

| Column | Line | |
|--------|------|---|
| 20 | 58 | Change "Taq" to --*Taq*--. |
| 21 | 59 | Change "Taq" to --*Taq*--. |
| 21 | 65 | Change "Taq" to --*Taq*--. |
| 22 | 3 | Change "Taq" to --*Taq*--. |
| 25 | 10 | Change "gene-" to --gene."--. |
| 25 | 11 | Before "FASEB" delete ".". |
| 29 | 61 | After "length" insert --,--. |
| 31 | 6 | After "length" insert --,--. |

Signed and Sealed this

Fourth Day of May, 1999

Attest:

Attesting Officer

Q. TODD DICKINSON
Acting Commissioner of Patents and Trademarks